United States Patent [19]

Naef

[11] Patent Number: 5,747,506
[45] Date of Patent: May 5, 1998

[54] ISOQUINOLINE COMPOUNDS, COMPOSITIONS CONTAINING THEM AND THEIR PHARMACEUTICAL USES

[75] Inventor: Reto Naef, Rheinfelden, Switzerland

[73] Assignee: Novartis AG, Basel, Switzerland

[21] Appl. No.: 771,556

[22] Filed: Dec. 20, 1996

Related U.S. Application Data

[63] Continuation of Ser. No. 472,042, Jun. 6, 1995, abandoned, which is a continuation of Ser. No. 333,699, Nov. 3, 1994, abandoned.

[30] Foreign Application Priority Data

Nov. 5, 1993 [GB] United Kingdom ............ 9322828

[51] Int. Cl.$^6$ .................... C07D 217/16; A61K 31/47
[52] U.S. Cl. ............................ 514/307; 546/144
[58] Field of Search .................... 546/144; 514/307

[56] References Cited

U.S. PATENT DOCUMENTS

| | | | |
|---|---|---|---|
| 3,878,215 | 4/1975 | Houlihan et al. | 260/283 |
| 3,891,654 | 6/1975 | Valette | 260/283 |
| 4,018,927 | 4/1977 | Voorhees | 424/260 |
| 4,547,508 | 10/1985 | Jonz et al. | 546/144 |
| 4,785,104 | 11/1988 | Rabloczky et al. | 546/144 |
| 4,980,359 | 12/1990 | Hasspacher et al. | 514/307 |
| 5,177,085 | 1/1993 | Naef | 514/307 |

FOREIGN PATENT DOCUMENTS

| | | | |
|---|---|---|---|
| 2213482 | 8/1989 | Denmark | 514/307 |
| 251361 | 1/1988 | European Pat. Off. | |
| 13672765 | 4/1964 | France | |
| 645139 | 10/1950 | United Kingdom | |

OTHER PUBLICATIONS

Heterocycles, vol. 9, No. 1, pp. 1–6 (1978).
J.Med. Chem., vol. 22, No. 4. pp. 348–352 (1979).
Exp. Toxic. Pathol., vol. 45, No. 8, pp. 473–479 (1994).

*Primary Examiner*—Zinna Northington Davis
*Attorney, Agent, or Firm*—Joseph J. Borovian

[57] ABSTRACT

Compounds of formula I

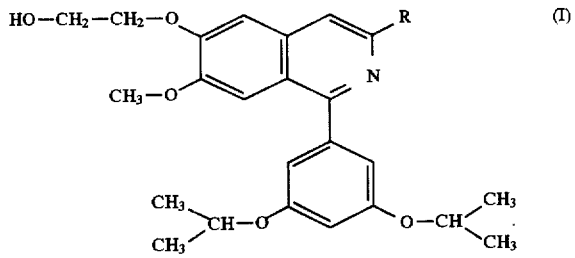

their physiologically-hydrolyzable and -acceptable esters and salts thereof. Said compounds, esters and pharmaceutically acceptable acid addition salts are useful as pharmaceuticals, e.g. for asthma therapy.

16 Claims, No Drawings

ISOQUINOLINE COMPOUNDS, COMPOSITIONS CONTAINING THEM AND THEIR PHARMACEUTICAL USES

This is a continuation of application Ser. No. 08/472,042, filed Jun. 6, 1995, now abandoned, which in turn is a continuation of application Ser. No. 08/333,699, filed Nov. 3, 1994, now abandoned.

The present invention relates to novel isoquinolines, processes for their production, their use as pharmaceuticals and pharmaceutical compositions comprising them.

More particularly the present invention provides, in a first aspect, a compound of formula I

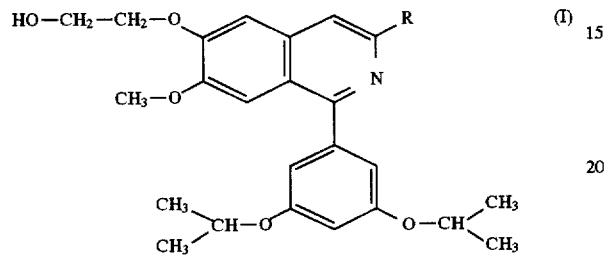

wherein R is ethyl or n-propyl, or a physiologically-hydrolyzable and -acceptable ester thereof, or an acid addition salt of such a compound or ester.

R in formula I is preferably ethyl.

By "physiologically-hydrolyzable and -acceptable ester" as used herein is meant an ester in which the hydroxy group of the formula I compound is esterified and which is hydrolyzable under physiological conditions to yield an acid which is itself physiologically tolerable at dosages to be administered. The term is thus to be understood as defining regular pro-drug forms. Examples of such esters include, for example, the acetates and benzoates of the formula I compounds.

Compounds of formula I and their esters as aforesaid exist in both free and acid addition salt form. Suitable pharmaceutically acceptable acid addition salt forms for pharmaceutical use in accordance with the present invention include, for example, the hydrochloride, hydrogen fumarate, hydrogen maleate and hydrogen-oxalate salts.

Compounds, esters and salts of the present invention are within the ambit of the invention disclosed and defined in UK patent no. 2 213 482, U.S. Pat. No. 4,980,359 and corresponding patents and applications world-wide. The compounds, esters and salts of the present invention are novel and, compared with compounds, esters and salts specifically disclosed in the aforesaid patents, exhibit surprisingly advantageous properties, in particular in relation to their intended pharmaceutical usage, e.g. as hereinafter described.

In a further aspect the present invention provides a process for the production of a compound of formula I as defined above or a physiologically-hydrolyzable and -acceptable ester thereof, or an acid addition salt of such a compound or ester, which process comprises:

a) for the production of a compound of formula I, deprotecting and/or dehydrogenating a compound of formula II

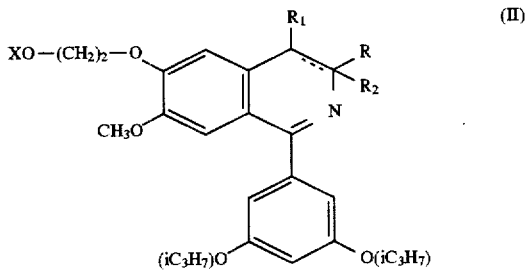

wherein R has the meaning given for formula I and X is hydrogen and $R_1$ and $R_2$ represent an additional bond as indicated by the dotted line or X is a hydroxy protecting group and $R_1$ and $R_2$ are each hydrogen or represent an additional bond as indicated by the dotted line;

b) for the production of a physiologically-hydrolyzable and -acceptable ester of a compound of formula I, esterifying a compound of formula I, and recovering the product of step a) or b) in free or acid addition salt form.

Removal of hydroxy protecting groups/dehydrogenation in accordance with process step a) may be performed in accordance with methods known in the art. Conveniently process step a) will involve both deprotection and dehydrogenation, e.g. employing a compound of formula II in which X is a benzyl protecting group and $R_1$ and $R_2$ are each hydrogen and effecting cleavage of the benzyl group and dehydrogenation in a one-pot reaction, for example by treatment with a palladium/charcoal catalyst at elevated temperature, under an inert atmosphere in an inert solvent or diluent, e.g. as hereinafter described in example 1.

Esterification in accordance with process step (b) may also be conducted in accordance with standard procedures, e.g. by reaction of a compound of formula I with an appropriate acid halide or anhydride in the presence of a base, for example an amine or alkali metal carbonate. Reaction is suitably carried out in an inert solvent or diluent, e.g. at a temperature of from 0° to 120° C., under an inert atmosphere.

The starting materials for the above process step (a) may be prepared according to the following reaction scheme

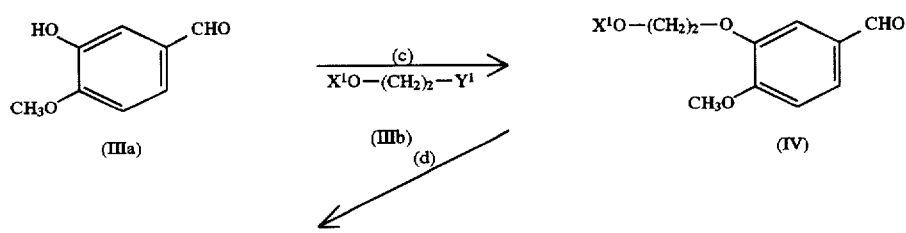

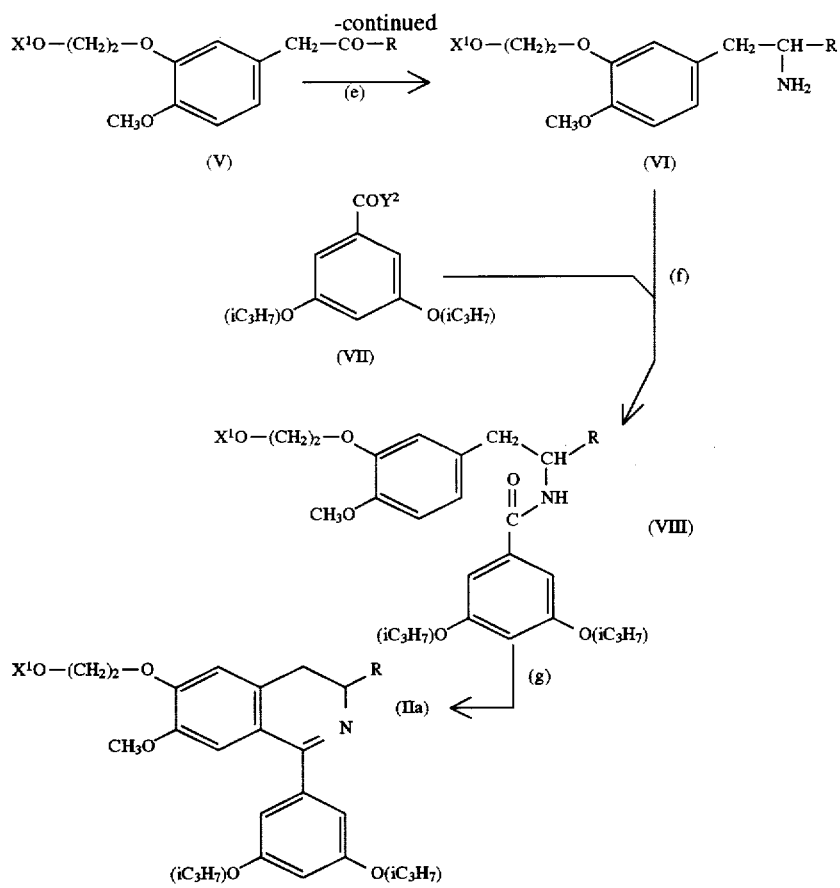

wherein $X^1$ is a hydroxy-protecting group, e.g., benzyl, $Y^1$ and $Y^2$ are each leaving groups and R has the meaning given for formula I. Suitable leaving groups as $Y^1$ are e.g. iodine or tosyl, whereby tosyl may be preferable for larger scale production. $Y^2$ is suitably chlorine. Steps (c) through (g) may be carried out in accordance with standard procedures, e.g. as described in the accompanying examples. Deprotection of compounds of formula IIa provides compounds of formula II in which X is hydrogen. Dehydrogenation of compounds of formula IIa provides compounds of formula II in which $R_1$ and $R_2$ together represent an additional bond.

Compounds of formulae IIIa, IIIb and VII are commercially available, known from the art or may be prepared analogously to the known compounds. Thus compounds of the formula VII may be prepared starting from 3,5-dihydroxybenzoic acid methyl ester by first alkylating this with isopropyl iodide in the presence of a base such as $K_2CO_3$ using e.g. methylethylketone as solvent, hydrolyzing the obtained 3,5-di-isopropoxy benzoic acid methyl-ester, e.g. by treatment with NaOH in methanol as solvent, and thereafter, converting the obtained 3,5-di-isopropoxy benzoic acid, e.g. to a corresponding acid halide, e.g. the acid chloride, for example by reaction with $SOCl_2$.

The following examples are illustrative of the method of the present invention.

EXAMPLE 1

Preparation of 1-(3,5-diisopropoxyphenyl)-3-ethyl-6-(2-hydroxyethoxy)-7-methoxy-isoquinoline
(Formula I : R=—$C_2H_5$ i) Process step (a)—deprotection and dehydrogenation:

13.5 g of 6-benzyloxyethoxy-1-(3,5-diisopropoxyphenyl)-3-ethyl-7-methoxy-3,4-dihydro-isoquinoline (Formula IIa: $X^1$=benzyl, R=ethyl), 1.3 g of Pd/C (10%) and 500 ml decahydronaphthalene are stirred for 5 hrs. at 200° C. under argon. The reaction mixture is cooled to room temperature filtered over Hyflo and washed with ethyl acetate. The decahydronaphthalene is distilled off at 50° C. under vacuum and the obtained product purified chromatographically on silica gel (e 0.04–0.06 mm) to yield the title compound:

m.p. free base=116°–118° C.
hydrochloride=218°–222° C.
hydrogen fumarate=82.5° C.
hydrogen oxalate=106°–107° C.
hydrogen maleate=87°–96° C.

The starting materials for the above process may be prepared as follows:

ii) 3-(2-Benzyloxyethoxy)-4-methoxy-benzaldehyde (Formula IV: $X^1$=benzyl)

20 g isovanillin (Formula IIIa), 41.3 g 2-benzyloxyethyl iodide (Formula IIIb) and 21.8 g potassium carbonate in 200 ml ethyl methyl ketone are stirred for 12 hrs. under reflux. The obtained suspension is cooled to room temperature and the precipitate filtered off, washed with acetone and evaporated. The residue is taken up in ethyl acetate and extracted with $H_2O$ (3×) and brine (1×). The organic phase is dried, filtered and evaporated to yield the title compound as an oil.

iii) 3-(2-Benzyloxyethoxy)-4-methoxybenzyl ethyl ketone (Formula V:$X^1$=benzyl, R=ethyl)

24 g of the product of step (ii) 21.5 g bromobutyric acid ethyl ester and 30 ml t.butyl methyl ether are added dropwise over 50 mins. at 5° C. to a pre-prepared suspension of sodium methylate in 25 ml t.butyl methyl ether. The reaction mixture is stirred for 45 mins. at ca. 5° C. and then stirred for 12 hrs. at room temperature. The pH is adjusted to 5 by addition of glacial acetic acid and the obtained suspension diluted with $H_2O$ and extracted 3× with t.butyl methyl ether. The organic phase is extracted with $NaHCO_3$ (1×) and brine (1×), and evaporated to ca. 100 ml. 13.5 ml 50% aqueous NaOH are added drop-wise and the whole stirred for 2 hrs. at 40° C., diluted with 50 ml. $H_2O$ and stirred for a further 30 mins. at room temperature. The organic phase is separated and the aqueous phase adjusted to pH 1 at max. 40° C. with 15 ml conc. HCl. The reaction mixture is stirred at 40° C. for a further 1.5 hrs., cooled to room temperature and extracted with toluene. The organic phase is washed with $NaHCO_3$ and brine, dried over $Na_2SO_4$, filtered and evaporated to yield the title compound as an oil.

iv) 1-[3-(2-Benzyloxyethoxy)-4-methoxyphenyl]-2-aminobutane (Formula VI : $X^1$=benzyl, R=ethyl)

20.6 g of the product of step (iii), 48.4 g ammonium acetate and 3.9 g sodium cyanoborohydride in 235 ml $CH_3OH$ in the presence of 12.1 g of 0.4 mm (4A) molecular sieve are stirred overnight at room temperature under an inert atmosphere. The reaction mixture is filtered over Hyflo and washed with $CH_3OH$. The filtrate is concentrated, the residue taken up in ethyl ether and extracted with 15% NaOH, $H_2O$ and saline. The organic phase is dried over $Na_2SO_4$, filtered and evaporated to yield the title compound as an oil.

v) N-(3,5-Diisopropoxybenzoyl)-1-[3-(2-benzyloxyethoxy)-4-methoxyphenyl]-2-aminobutane (Formula VIII: $X^1$=benzyl, R =ethyl)

19.9 g 3,5-diisopropoxy benzoyl chloride in 100 ml $CH_2Cl_2$ are added dropwise over 1.5 hrs. to 17.0 g of the product of step (iv), 15.6 g triethylamine and 630 mg N,N-dimethylaminopyridine in 150 ml $CH_2Cl_2$ and the reaction mixture is stirred for 12 hrs. at ca. 0° to room temperature. The obtained mixture is concentrated, the residue taken up in ethyl acetate and extracted with 1N HCl, 10% $NaHCO_3$ solution and brine. The organic phase is dried over $Na_2SO_4$, filtered and concentrated. The residue, which commences to crystallize, is diluted with ethyl ether and filtered to yield the title compound. This is used for further reaction without additional purification.

vi) 6-Benzyloxyethoxy-1-(3,5-diisopropoxyphenyl)-3-ethyl-7-methoxy-3,4-dihydroisoquinoline 15.3 g of the product of step (v) and 12.4 g $POCl_3$ in 250 ml acetonitrile are stirred for 5 hrs. under reflux. The reaction mixture is concentrated, the residue taken up in ethyl acetate and extracted with $Na_2CO_3$ solution and brine. The organic phase is dried over $Na_2SO_4$, filtered and evaporated and the residue purified chromatographically on silica gel (e 0.04–0.63 mm) to yield the title compound as an oil.

EXAMPLE 2

Preparation of 1-(3,5-diisopropoxyphenyl)-6-(2-hydroxyethoxy)-7-methoxy-3-n.propyl-isoquinoline (Formula I R=n.propyl)

The title compound is prepared analogously to Example 1: free base obtained as a foam: hydrogen oxalate m.p.= 154°–156° C.

Compounds of formula I, physiologically-hydrolyzable and -acceptable esters thereof and pharmaceutically acceptable acid addition salts of said compounds and esters (hereinafter collectively: AGENTS OF THE INVENTION) exhibit pharmacological activity and are useful as pharmaceuticals, e.g. for therapy, in the treatment of diseases and conditions as hereinafter set forth.

In particular AGENTS OF THE INVENTION exhibit cyclic nucleolide phosphodiesterase (PDE) isoenzyme inhibiting activity, selective for type IV isoenzyme and with markedly and surprisingly greater type IV specificity than for known compounds, for example as disclosed in the aforementioned UK and U.S. Pat. Nos. 2,213,482 and 4,980, 359.

AGENTS OF THE INVENTION posess anti-inflammatory, anti-airways hyperreactivity and bronchodilator properties. They further posess immunosuppressive, TNFA secretion inhibitory and other pharmacological activities as may be demonstrated in standard test methods for example as follows:

[All experiments described below are suitably done using the hydrogen-oxalate salt of the test compound, e.g. compound of example 1. In the case of the example 1 compound a stable 30 mM stock solution of the hydrogen-oxalate salt may be prepared with 10% Tween in 80% abs. $C_2H_5OH$. For pharmacological experiments it should be diluted at least 1:10,000.]

PDE ISOENZYME INHIBITION

TEST A: Human PDE Isoenzyme Inhibition Assay

All isoenzyme preparations are derived from human sources. Type III and IV preparations are obtained taking advantage of the predominance of type III isoenzymes in platelets and of type IV isoenzymes in neutrophils applying the following techniques:

Cells and tissues are homogenized on ice in tris-HCl 10 mM pH 7.4 containing: Sucrose (250 mM), EDTA 1 mM, dithiothreitol (1 mM), leupeptin and pepstatin A (1 µg/ml each), and phenyl-methyl-sulphonyl fluoride (PMSF, 0.17 mg/ml added just before the homogenization). Neutrophils (type IV) and platelets (types II and III) are obtained from human blood and sonicated (Branson probe, 4×15 sec.). Human lung (types I and V) is obtained from patients undergoing surgery and homogenized using a Polytron homogenizer (two bursts of 30 sec).

Isoenzyme preparations: PDE III and IV (substrate cAMP 1 µM) preparations consist of low-speed supernates of the platelet and neutrophil homogenates, respectively. Types I (substrate cAMP 1 µM, $Ca^{2+}$ 0.5 mM, calmodulin 125 nM), II (cAMP 100 µM) and V (cGMP 1 µM) are separated by anion-exchange chromatography (Q-Sepharose) using a gradient of NaCl in homogenization buffer without sucrose and PMSF (0 to 0.1M NaCl in 2.5 column volumes, 0.1 to 0.45M in 24 column volumes). PDE I: fractions where hydrolysis of cAMP 1 µM can be stimulated by $Ca^{2+}$+calmodulin (0.5 mM and 125 nM, respectively); eluting at 0.17–0.18M NaCl. PDE II: fractions showing substantial cAMP hydrolytic activity at 100 µM but not at 1 µM; eluting at 0.31–0.32M NaCl. PDE V: fractions selectively hydrolyzing cGMP 1 µM over cAMP 1 µM; eluting at 0.20–0.24M NaCl.

PDE activity is assayed in the presence and absence of test substance at varying concentration using the ion-exchange column method described by Thompson et al., Nucleotide Res., 10, 69–92 (1979), with 1 µM [$^3$H]-cyclic AMP as substrate.

In this test method AGENTS OF THE INVENTION predominantly inhibit PDE isoenzymes of types III, IV and V having relatively little effect in relation to types I and II. Within the III, IV, V grouping, AGENTS OF THE INVENTION exhibit markedly increased selectivity for inhibition of PDE isoenzymes of type IV in comparison with other known PDE isoenzyme inhibitors and are characterizable as type IV isoenzyme specific. Thus in one test run, the compound of example 1 in hydrogen oxalate salt form is found to have at least 180 fold greater activity in inhibiting the type IV isoenzyme than other isoenzyme preparations tested.

ANTI-INFLAMMATORY ACTIVITY

TEST B: Inhibition of Eosinophil Activation by formyl-MetLeuPhe (fMLP)

Purified human eosinophils ($10^4$/well in 0.2 ml HBSS) are stimulated with fMLP (1 µM) in the presence of lucigenin (25 µM). Inhibition of the oxidative burst (measured as changes in chemiluminescence) is determined from dose response curves using the logistic equation.

AGENTS OF THE INVENTION are active in the above test method at concentrations of the order of from 0.001 to 0.5 µM.

TEST C: Inhibition of TNFα Secretion

900 µl THP-1 cells (0.5 $10^6$ cells together with 100 U γ-interferon/0.9 ml) are pipetted into 24 well culture plates and followed by 100 µl test substance. After 3 hours at 37° C. in 5% $CO_2$/95% air, 10 µl LPS 5 µg/ml is added and the incubation continued for a further 40 hours. Appropriate controls are also included. The media are then removed and clarified by centrifugation at 1000 g for 10 min. 1.0 ml digitonin 0.01% is added to the wells to lyse the cells which are loosened by scraping with a rubber policeman and left at 4° C. for 10 min. Lactate dehydrogenase measurements are then performed immediately and the samples stored at –200° C. until the other determinations can be performed. The assays are: IL-1β (medium), TNF-α (medium), and DNA (lysates). IL-1β, and TNF-α assays are determined using commercially available ELISA kits.

The method of Kapuscinski et al Anal. Biochem. (83, 252–257 (1977) is used to assay DNA. 300 µl samples of cell lysate in 0.01% digitonin are mixed with 750 µl tris-HCl buffer pH 7.0 (containing 13.2 mM $Na_2SO_4$), 300 µl $H_2O$ and 150 µl DAPI (4',6-diamidino-2-phenylindole.2HCl) 2 µg/ml. The fluorescence is then measured at 372 nm (excitation) and 454 nm (emission) using a Perkin Elmer 3000 fluorimeter. The samples are read against a standard curve of calf thymus DNA (0.5 to 10 µg/ml) run at the same time.

Lactate dehydrogenase is assayed as follows: 50 µl samples (medium or cell lysate in 0.01% digitonin) are added to 96 well microtitre plates followed by 200 µl of 0.3 mM NADH/1 mM sodium pyruvate in 62 mM sodium phosphate buffer pH 7.5. The plate is mixed gently using a mechanical microtitre plate shaker and placed in a Twin-reader spectrophotometer (Flow Laboratories). The mex-tinction values at 340 nm are measured automatically at 1 minute intervals over an 11 minute period and the enzyme rate calculated automatically using a computer program. Since enzyme activity is lost on freezing and thawing, assays are performed on fresh samples.

Test compounds are added with the γ-IFN at varying concentration and remain with the cells throughout the course of the experiment.

In the above test method AGENTS OF THE INVENTION exhibit potent inhibition of TNFα at concentrations of the order of from 0.001 to 0.5 µM. Inhibition of IL-1β is observed only at significantly greater concentration.

TEST D: Inhibition of SRS-A Production

Guinea-pigs are passively sensitized 24 hrs. prior to testing by i.v. administration of 1 ml homologous anti-ovalbumin antiserum. Prior to antigen challenge test animals are pre-treated with 0.32 mg/kg propanol i.v. (inhibition of endogenous catecholamines), 3.2 mg/kg, i.v. mepyramine (H1 receptor antagonism) and 3.2 mg/kg, i.v. indomethacin (inhibition of cyclo-oxygenase). Allergen challenge is effected by administration of 32 µg/kg, ovalbumin i.v. and the resultant constrictor response on airways resistance used as a functional read out of SRS-A activity. Separate test groups receive 10 mg/kg, i.v. FPL 55712 (an $LTD_4$ receptor antagonist) 1 minute prior to challenge or test substance at varying dosage. i.v. by infusion, beginning 16 minutes prior to challenge. Groups receiving FPL 55712 exhibit abolition of bronchoconstriction, confirming the action of SRS-A as mediator in the response.

In the above test method AGENTS OF THE INVENTION inhibit SRS-A production as evidenced by reduction of constrictor response at dosages of the order of 5 to 100 µg/kg/min. infused i.v..

TEST E: Bacterial Endotoxin [LPS] Induced Lethality in the Guinea Pig

Guinea-pigs are anesthetized by intraperitoneal injection of sodium phenobarbitone (100 mg/kg.) supplemented with sodium pentobarbitone (30 mg/kg) and paralyzed by intramuscular injection of gallamine (10 mg/kg). Animals are ventilated (8 ml/kg, 1 Hz) with a mixture of air and oxygen (40:60, v/v) via a tracheal cannula. Ventilation is monitored at the trachea by a pneumotachograph connected to a differential pressure transducer. Coincident pressure changes within the thorax are measured via an intrathoracic cannula, using a differential pressure transducer, so that the pressure difference between the trachea and thorax can be measured and displayed. Blood pressure and heart rate are recorded from the carotid artery using a pressure transducer and a cannula is introduced into the right jugular vein to allow intravenous infusion of test substance min prior to and concomitantly with infusion of LPS at a constant rate (3.0 ml/hr to give 10 mg/kg/hr) from an infusion pump. The left jugular vein is cannulated for administration of (±) propranolol (1 mg/kg) injected as an intravenous bolus. From measurements of air-flow and transpulmonary pressure, both $R_L$ and $C_{dyn}$ are calculated after each respiratory cycle using a digital electronic pulmonary monitoring system which displays blood pressure, intrathoracic pressure and airflow and computes $R_L$ and $C_{dyn}$ in real time for display on a visual display unit. Experimental data is stored continuously and, on termination of an experiment, experimental traces or processed data are plotted.

Infusion of [±propanolol] ensures consistent susceptibility to LPS. In anesthetized animals pre-treated with [±] propanalol, infusion of LPS in the above model induces progressive airway obstruction. Death consequential to endotoxin shock usually occurs within ca. 1 hr of terminating LPS infusion.

In the above test model, administration of AGENTS OF THE INVENTION at dosages of the order of 1 to 500 µg/kg/min. i.v. protects animals against endotoxin (LPS) induced airways obstruction during the course of the experiment) as well as LPS induced lethality.

TEST F: Arachidonic Acid Induced Irritant Contact Dematitis in the Mouse

Female NMRI mice (ca. 30 g) are treated topically on both the inner and outer aspects of the right ear with 10 µl dimethylsulfoxide: acetone: ethanol (2:4:4) containing test compound at varying concentration. After 30 mins. the right ear is treated topically inside and out with 1 mg arachidonic acid in 10 µl acetone. Animals are sacrificed after 30 mins., the ears amputated at the cartilage line and weighed. The difference in weight between left and right ears is calculated and % inhibition determined relative to a control group receiving arachidonic acid treatment only.

AGENTS OF THE INVENTION inhibit contact dermatitis in the above test model on application at concentration of the order of from 3.0 to 300 nM.

BRONCHODILATOR ACTIVITY
TEST G: Relaxation of Human Bronchus

Samples of human lungs disected during surgery for cancer are obtained within 3 days after removal. Small bronchi (inner diameter≈2 to 5 mm are excised, cut into segments and placed in 2 ml Liquid Nitrogen Storage Ampoules filled with foetal calf serum (FCS) containing 1.8M dimethyl sulphoxide (DMSO) and 0.1M sucrose as cryoprotecting agents. The ampoules are placed in a polystyrol box (11×11×22 cm) and slowly frozen at a mean cooling rate of about 0.6° C./min in a freezer maintained at −70° C. After 3–15 h the ampoules are transferred into liquid nitrogen (−196° C.) where they are stored until use. Before use the tissues are exposed for 30–60 min to −70° C. before being thawed within 2.5 min by placing the ampoules in a 37° C. water bath. Thereafter the bronchial segments are rinsed by placing in a dish containing Krebs-Henseleit solution (composition mM: NaCl 118, KCl 4.7, $MgSO_4$ 1.2, $CaCl_2$ 1.2, $KH_2PO_4$ 1.2, $NaHCO_3$ 25, glucose 11, EDTA 0.03) at 37° C., cut into rings and suspended in 10 ml organ baths for isometric tension recording under a preload of about 1 g. Concentration-response curves are produced by cumulative additions, each concentration being added when the maximum effect has been produced by the previous concentration. Papaverine (300 µM) is added at the end of the concentration-response curve to induce complete relaxation of the bronchial rings. This effect is taken as 100% relaxation.

In the above test model AGENTS OF THE INVENTION produce concentration-related relaxation of human bronchus ring preparations at concentrations of from 0.001 to 1.0 µM.

TEST H: Suppression of SRS-A Induced Bronchoconstriction

Guinea pigs (Dunkin-Hartley, male, 400–600 g) are anesthethized with phenobarbital (100 mg/kg i.p.) and pentobarbital (30 mg/kg i.p.) and paralyzed with gallamine (100 mg/kg i.m.) Animals are ventilated via a tracheal cannula (8 ml/kg, 1 Hz) with a mixture of air and oxygen (45:55 v/v). Blood pressure and heart rate are recorded at the carotid artery. Ventilation is monitored by a Fleisch flow transducer in line with the inspiratory circuit. When making measurements of flow, coincident pressure changes in the thorax are monitored directly via an intrathoracic trochar, permitting display of differential pressure relative to the trachea. From this information in relation to flow and differential pressure, resistance $[R_L]$ and compliance $[C_{dyn}]$ are calculated using a digital respiratory analyzer for each respiratory cycle.

Test animals are passively sensitized 24 hrs. prior to testing by administration of homologous anti-ovalbumin antiserum (1 ml i.v.). Prior to allergen challenge, animals are pretreated with proprandolol (0.32 mg/kg i.v.) to inhibit the effects of endogenous catecholamines, mepyramine (3.2 mg/kg i.v.) to block histamine $H_1$ receptors and indomethacin (3.2 mg/kg i.v.) to inhibit cyclooxygenase. Allergen challenge is achieved by administration of ovalbumin (OA) and the resultant bronchoconstrictor response is used as a functional read-out of SRS-A activity.

Two experiments are performed:

1) In the first, animals are challenged with OA (32 mg/kg i.v.) and the effects of the leukotriene $D_4$ receptor antagonist FLP 55712 (10 mg/kg i.v., 1 min. prior to OA challenge) and test compound (1, 10 and 100 mg/kg/min. given as an i.v. infusion starting 15 mins. prior to OA challenge) investigated.

2) In the second, animals are challenged with OA (1.0 or 1.8 mg/ml inhaled over 60 breaths) and the effect of test compound, administered at varying dosage directly into the lung by tracheal instillation, is measured.

In experiment 1), the bronchoconstrictor effect of OA is abolished following administration of FPL 55712 consistent with mediation of the response by SRS-A. AGENTS OF THE INVENTION exhibit dose-dependent inhibition of bronchoconstrictor response.

In experiment 2), AGENTS OF THE INVENTION exhibit inhibitory activity at dosages of the order of from 0.001 to 10 mg/kg/min. via tracheal instillation.

TEST I. Suppression of Bombesin Induced Bronchoconstriction

Animals (Guinea pigs) are prepared as described above for TEST H.

Bombesin is administered by constant i.v. infusion at 100 mg/kg/min., thereby causing sustained bronchospasm. Test substance is administered i.v. in saline or i.d. in ethanol/saline (1% v/w). Bronchodilator effect is measured at 1 and 3 mins. following i.v. administration or 16 and 64 mins. following i.d. administration and is expressed as the % inhibition of the initial response using $R_L$ as an index of lung function.

In the above test model AGENTS OF THE INVENTION exhibit marked bronchodilator activity at dosages of the order of from 0.001 to 0.1 mg/kg i.v. or 0.1 to 5.0 mg/kg i.d..

TEST J: Suppression of Methacholine (MeCH) Induced Broncho-Constriction in the Rhesus Monkey Male rhesus monkeys (body weight 10.3–13.2 kg) are anesthetized with ketamine (20 mg/kg i.m., initial) and maintained with thiopental (8 mg/kg/h i.v.) via an indwelling catheter in the left saphenous vein, throughout the experimental procedure. Animals are allowed to breathe spontaneously, and are placed in the left lateral incumbent position. The larynx, eppiglottis and pharynx are anesthetized (topical xylocaine) allowing introduction and placement of a cuffed 4.5 mm pediatric endotracheal tube.

MeCH is administered as an aerosol (saline vehicle: aerosol generated by a nebulizer operated under an airflow of 6 l/min, mean particle size of 3.5 µm) with a 2 minute exposure, tidal breathing. All tests employ a 0.6 mg/ml solution or 2.5 mg/ml solution in the case of poor MeCH responders. MeCH bronchoconstrictor tests are spaced 30 min apart, with administration of test substance (in a lactose vehicle suspension, 1 mg/ml, 1 ml administered under bronchoscopic control, 1 cm above the carina) 15 min prior to MeCH challenge.

Test substance is administered in a cumulative manner. Bronchodilator activity is estimated as the % inhibition of bronchoconstrictor response to MeCH on resistance.

AGENTS OF THE INVENTION are active in the above test model on administration at dosages of the order of from 10 to 500 ng/kg.

SUPPRESSION OF AIRWAYS HYPERREACTIVITY
TEST K: Immune Complex Induced Hyperreactivity in the Guinea-Pig Guinea-pigs are a anesthetized and prepared for recording of lung-function as for TEST F above. Allergic reaction is induced by i.v. administration of preformed immune complexes (prepared by addition of 30 µg bovine γ-globulin in 0.05 ml saline to 0.05 ml guinea-pig anti-bovine γ-globuline anti-serum) 3× at 10 min. intervals. Subsequent i.v. administration of histamine (1–3.7 µg/kg at 10 min. intervals) enables definition of sensitivity of the airways prior to and post administration of immune complex. Airways hyperreactivity is expressed as the paired difference for the maximal value of $R_L$ in response to histamine before and after administration of immune complex. Test compounds are administered intratracheally (i.t.) at varying dosage subsequent to induction of hyperreactivity.

AGENTS OF THE INVENTION are active in abolishing or restricting airways hyperreactivity in the above test method or administration at dosages of the order of from 0.5 to 50.0 µg/kg i.t..

IMMUNO SUPPRESSIVE ACTIVITY

TEST L: Murine Mixed Lymphocyte Reaction

Ca. $0.5\times10^6$ lymphocytes from the spleen of female (8–10 weeks) Balb/c mice are incubated for 5 days in 0.2 ml cell growth medium with ca. $0.5\times10^6$ lymphocytes from the spleen of female (8–10 weeks) CBA mice. Test substance is added to the medium at various concentrations. Activity is assessed by ability to suppress proliferation associated DNA synthesis as determined by incorporation of radiolabelled thymidine.

AGENTS OF THE INVENTION inhibit thymidine incorporation at concentrations of the order of from 0.1 to 50.0 nM.

AGENTS OF THE INVENTION are also found to inhibit the in vitro proliferative responses of human peripheral blood mononuclear cells e.g. to tuberculin and, in particular, to exhibit synergetic inhibitory effect in conjunction with immunosuppressively active agents, for example immunosuppressive cyclosporins such as cyclosporin A, and corticosteroids.

In addition to the foregoing, general pharmacological testing indicates that AGENTS OF THE INVENTION exhibit a marked and surprisingly improved profile in relation to intended therapeutic use as further set forth below, as compared with previously known compounds, for example reduced influence on behavioral response and/or, in particular, reduced cardiovascular effect in relation to hemodynamic parameters (influence on heart rate, induction of vasoconstriction etc.).

Thus in a series of experiments using the Doppler aortic flow test in the rabbit [J. Pharmacol. Meth. 24, 263–267 (1990)], the compound of example 1 in hydrogen-oxalate acid addition salt form is observed to exhibit no cardiovascular side effects at dosages e.g. up to the order of 0.3 mg/kg, and only slight decrease in heart rate (due to vasoconstriction) at dosages of the order of 1 mg/kg.

Similarly the same compound in hydrogen-oxalate acid addition salt form is found to produce no or only minimal change in mean arterial pressure, heart rate and plasma glucose concentrations, e.g. on administration to conscious dogs at dosages, e.g. of up to 0.3 mg/kg i.v. or 0.6 mg/kg p.o., which give substantial and long-lasting inhibition of PDE IV added to plasma. All dosages are also generally well tolerated.

As already noted, AGENTS OF THE INVENTION are also characterized by marked and increased specificity as type IV PDE isoenzyme inhibitors. They are also characterized by a notably prolonged metabolic half-life/duration of action.

Having regard to their anti-inflammatory activity their influence on airways hyperreactivity and their profile in relation to PDE isoenzyme inhibition, in particular as selective type IV inhibitors, AGENTS OF THE INVENTION are useful for the treatment, in particular prophylactic treatment, of obstructive or inflammatory airways disease. Thus by continued and regular administration over prolonged periods of time AGENTS OF THE INVENTION are useful in providing advance protection against recurrence of bronchoconstrictor or other symptomatic attack consequential to obstructive or inflammatory airways disease or for the control, amelioration or reversal of basal status of such disease.

Having regard to their bronchodilator activity AGENTS OF THE INVENTION are useful as bronchodilators, e.g. for the treatment of chronic or acute broncho-constriction, e.g. for the symptomatic treatment of obstructive or inflammatory airways disease.

The words "treatment" and "treating" as used throughout the present specification and claims in relation to obstructive or inflammatory airways disease are to be understood accordingly as embracing both prophylactic and symptomatic modes of therapy.

In accordance with the foregoing the present invention further provides

A. A method
   a) for the treatment of airways hyperreactivity,
   b) of effecting bronchodilation or, in particular,
   c) of treating obstructive or inflammatory airways disease, in a subject in need thereof, which method comprises administering to said subject an effective amount of an AGENT OF THE INVENTION.

Obstructive or inflammatory airways diseases to which the present invention applies include asthma, pneumoconiosis, chronic obstructive airways or pulmonary disease (COAD or COPD) and adult respiratory distress syndrome (ARDS), as well as exacerbation of airways hyperreactivity consequent to other drug therapy, e.g. aspirin or β-agonist therapy.

The present invention is applicable to the treatment of asthma of whatever type or genesis, including intrinsic and, especially, extrinsic asthma. It is applicable to the treatment of allergic (atopic/IgE-mediated) asthma. It is also applicable to the treatment of non-atopic asthma, including e.g. bronchitic, exercise induced and occupational asthma, asthma induced following bacterial infection and other non-allergic asthmas. It is further applicable to the treatment of wheezy infant syndrome (infant, incipient asthma).

The invention is applicable to the treatment of pneumoconiosis of whatever type or genesis including, for example, aluminosis, anthracosis, asbestosis, chalicosis, ptilosis, siderosis, silicosis, tobacoosis and byssinosis.

The invention is applicable to the treatment of COPD or COAD including chronic bronchitis, pulmonary emphysema or dyspnea associated therewith.

The invention is also applicable to the treatment of bronchitis of whatever type or genesis including, e.g. acute, arachidic, catarrhal, chronic, croupus or phthinoid bronchitis etc..

Having regard to their activity as selective inhibitors of TNF-α release, AGENTS OF THE INVENTION are also useful for the down-regulation or inhibition of TNF-α release, e.g. for the treatment of diseases or conditions in which TNF-α release is implicated or plays a mediating role, e.g. diseases or conditions having an aetiology involving or comprising morbid, for example undesirable, excessive or unregulated TNF-α release, in particular for the treatment of cachexia or endotoxin shock and in treatment of AIDS [cf. Sharief et al. Mediators of Inflammation, 1 323–338 (1992)].

The method of the invention is applicable to the treatment of cachexia associated with morbid TNF-α release or TNF-α blood-serum levels of whatever origin, including cachexia consequential to, e.g. bacterial, viral or parasitic, infection or to deprivation or deterioration of humoral or other organic, e.g. renal function. It is for example applicable to the treatment of cancerous, malarial and vermal cachexia, cachexia resulting from dysfunction of the pituitary, thyroid or thymus glands as well as uremic cachexia. It is in particular applicable to the treatment of AIDS-related cachexia, i.e. cachexia consequential to or associated with to HIV infection.

The method of the invention is also applicable to the treatment of endotoxin shock. In this regard it is to be noted that the present invention provides a method for the treatment of endotoxin shock as such as well as of conditions consequential to or symptomatic of endotoxin shock, for example ARDS (adult respiratory distress syndrome).

The method of the invention is further applicable to the treatment of disease consequential to HIV infection, e.g. AIDS, e.g. to the amelioration or control of the advance of such disease.

Having regard to their profile in relation to inhibition of PDE isoenzymes and/or TNFα release inhibition, as well as their immunosuppressive activity, AGENTS OF THE INVENTION are also useful as immunosuppressive agents, e.g. for the treatment of autoimmune diseases, in particular for the treatment of autoimmune diseases in which inflammatory processes are implicated or which have an inflammatory component or aetiology, or as anti-inflammatory agents for the treatment of inflammatory disease in particular for the treatment of inflammatory disease in which autoimmune reactions are implicated or having an autoimmune component or aetiology.

Examples of such disease to which the present invention is applicable include autoimmune hematological disorders (e.g. hemolytic anemia, aplastic anemia, pure red cell anemia and idiopathic thrombocytopenia), systemic lupus erythematosus, polychondritis, sclerodoma, Wegener granulamatosis, dermatomyositis, chronic active hepatitis, myasthenia gravis, Steven-Johnson syndrome, idiopathic sprue, autoimmune inflammatory bowel disease (e.g. ulcerative colitis and Crohn's disease) endocrine ophthalmopathy, Grave's disease, sarcoidosis, alveolitis, chronic hypersensitivity pneumonitis, multiple sclerosis, primary billiary cirrhosis, juvenile diabetes (diabetes mellitus type I), uveitis (anterior and posterior), keratoconjunctivitis sicca and vernal keratoconjunctivitis, interstitial lung fibrosis, psoriatic arthritis and glomerulonephritis (with and without nephrotic syndrome, e.g. including idiopathic nephrotic syndrome or minal change nephropathy), as well as inflammatory and/or hyperproliferative skin diseases such as psoriasis atopic dermatitis, pemphigus and, in particular, contact dermatitis, e.g. allergic contact dermatitis.

AGENTS OF THE INVENTION are in particular useful for the treatment of arthritis, and other rheumatic or inflammatory disease, especially for the treatment of rheumatoid arthritis.

As immunosuppressants AGENTS OF THE INVENTION are further indicated for use in the prevention of graft rejection, e.g. for the maintainance of allogenic organ transplants or the like, e.g. in relation to kidney, liver, lung, heart, heart-lung, bowel, bone-marrow, skin, or corneal transplant.

Having regard to their anti-inflammatory activity, in particular in relation to inhibition of eosinophil activation, AGENTS OF THE INVENTION are also useful for the treatment of eosinophil related disorders, e.g. eosinophilia, in particular eosinophil related disorders of the airways (e.g. involving morbid eosinophilic infiltration of pulmonary tissues) including hypereosinophilia as it effects the airways and/or lungs as well as, for example, eosinophil-related disorders of the airways consequential or concomitant to Loffler's syndrome, eosinophilic pneumonia, parasitic (in particular metazoan) infestation (including tropical eosinophilia), bronchopulmonary aspergillosis, polyarteritis nodosa (including Churg-Strauss syndrome), eosinophilic granuloma and eosinophil-related disorders affecting the airways occasioned by drug-reaction.

Having regard to their profile in relation to inhibition of PDE isoenzymes, in particular their profile as selective type IV inhibitors, AGENTS OF THE INVENTION are further useful as type IV PDE inhibitors, for example for the treatment of disease involving tissue calcium depletion, in particular degenerative diseases of the bone and joint involving calcium depletion, especially osteoporosis. In this regard they are further useful for the treatment of allergic inflammatory diseases such as rhinitis, conjunctivitis, atopic dermatitis, urticaria and gastro-intestinal allergies; as vasodilators, e.g. for the treatment of angina, hypertension, congestive heart failure and multi-infarct dementia; and for the treatment of other conditions where inhibition of PDE IV is indicated, for example, depression, conditions and diseases characterized by impaired cognitive function including Alzheimer's disease, Parkinson's disease and stroke.

Having regard to their ability to interact synergistically with immunosuppressive and/or anti-inflammatory drug substances, AGENTS OF THE INVENTION are also useful as co-therapeutic agents for use in conjunction with such drugs, e.g. as potentiators of therapeutic activity of such drugs or as means of reducing required dosaging or potential side effects of such drugs. Drug substances with which AGENTS OF THE INVENTION may suitably be co-administered include, e.g. cyclopeptide, cyclopeptolide or macrolide immunosuppressive or anti-inflammatory drug substances, for examples drugs belonging to the cyclosporin class, e.g. cyclosporins A or G, the drug substances tacrolimus (also known as FK 506), ascomycin and rapamycin and their various known congeners and derivatives, as well as glucocorticosteroid drugs. Diseases to which such co-therapy may be applied include e.g. any disease or condition requiring immunosuppressive or anti-inflammatory drug therapy, e.g. as hereinbefore set forth. In particular AGENTS OF THE INVENTION are suitable for use in co-therapy as aforesaid, e.g. for the purposes of immunosuppressive, anti-inflammatory or anti-asthmatic treatment, e.g. to achieve cyclosporin, e.g. cyclosporin A-, macrolide- or steroid-sparing effect.

In accordance with the foregoing the present invention also provides:

B. A method a) for the down-regulation or inhibition of TNF-α release, b) for the inhibition of PDE IV isoenzyme activity, c) of effecting immunosuppression, d) for the treatment of inflammatory disease, or e) for the treatment of any particular condition or disease as hereinabove set forth, in a subject in need thereof, which method comprises administering to said subject an effective amount of an AGENT OF THE INVENTION.

The present invention also provides:

C. An AGENT OF THE INVENTION for use as a pharmaceutical, for example for use in any method or in the treatment of any disease or condition as hereinbefore set forth, e.g. as defined under A or B above.

Dosages employed in practicing the present invention will of course vary depending, e.g. on the particular disease or condition to be treated, the particular AGENT OF THE INVENTION used, the mode of administration and the therapy desired. In general, however, satisfactory results, e.g. for the treatment of diseases as hereinbefore set forth are indicated to be obtained on oral administration at dosages of the order from about 0.01 to 2.0 mg/kg. In larger mammals, for example humans, an indicated daily dosage for oral administration will accordingly be in the range of from about 0.75 to 150 mg, conveniently administered 1× or in divided doses 2 to 4× daily or in sustained release form. Unit dosage forms for oral administration thus suitably comprise from about 0.2 to 75 or 150, e.g. from about 0.2 or 2.0 to 50, 75 or 100 mg AGENT OF THE INVENTION, together with a pharmaceutically acceptable diluent or carrier therefor.

For use in the treatment of chronic or obstructive airways disease, e.g. asthma AGENTS OF THE INVENTION are preferably administered by the inhaled route. Again dosages employed will vary, e.g. depending on the particular disease or condition, the particular AGENT OF THE INVENTION employed, the particular mode of administration (e.g. whether by dry powder inhalation or otherwise) and the effect desired. In general, however, an indicated inhaled daily dosage will be of the order of from about 2.5 to about 130.0 µg/kg/day e.g. from about 13.0 to about 60.0 µg/kg/day. For larger mammals, for example humans, an indicated daily dosage for administration by inhalation, e.g. in the treatment of asthma, will be in the range of from about 0.2 to about 10.0 mg, e.g. from about 1 to about 5 mg, conveniently given in one single administration or 2 or 3 separate administrations throughout the day. An appropriate dosage per administration will thus be of the order of from about 200 µg to about 3.3 mg, with administration up to 3 times daily, suitably administered from a dry powder inhalation delivery device in a series of 2 to 8 puffs at each administration.

AGENTS OF THE INVENTION may also be administered by any other appropriate route, e.g. by infusion, for example for the treatment of endotoxin shock; nasally, for example for the treatment of rhinitis; occularly, for example for the treatment of autoimmune diseases of the eye; dermally, i.e. topically to the skin, for example for the treatment of dermatosese or psoriasis; or rectally, e.g. via enemation or suppository, for example for the treatment of inflammatory bowel disease. Suitable dosages for application by such routes will generally be of the order of 10 to 100× less than those required for oral administration.

Pharmaceutical compositions comprising AGENTS OF THE INVENTION may be prepared using conventional diluents or excipients and techniques known in the galenic art. Thus oral dosage forms may include tablets, capsules and the like. Formulations for dermal administration may take the form of creams, ointments, gels, or transdermal delivery systems, e.g. patches and, in addition to inert diluents or carriers, may suitably contain skin penetration enhancing agents, again as known in the art.

Compositions for inhalation may comprise aerosol or other atomizable formulations as well as inhalable dry powder formulations, with or without diluent, for administration by any appropriate dry powder inhalation system as known in the art. For the preparation of dry powder forms for inhalation, compounds of formula I or physiologically-hydrolyzable and -acceptable esters thereof are suitably employed in pharmaceutically acceptable acid addition salt form. In the case of the compound of example 1, the hydrochloride salt (mp. 218°–222° C.) is in particular suitable. The said salt form is suitably milled, e.g. using an air-jet or ceramic mill to provide a finely divided inhalable powder, e.g. having an average particle diameter of ca. 2–3 µ. Appropriately at least 90% of the material will have an average particle diameter of less than 7.8 µ, more preferably of less than 4.8 µ. In order to ensure obtention of an appropriate and consistent particulate product suitable for administration by inhalation in dry powder from, it may be preferable to effect milling of the active ingredient, e.g. the hydrochloride salt of the example 1 product, premixed with an appropriate inhalable carrier medium, e.g. lactose, under conditions of reduced temperature.

In accordance with the foregoing the present invention also provides: a pharmaceutical composition comprising an AGENT OF THE INVENTION together with a pharmaceutically acceptable diluent or carrier therefor, e.g. for use in any method as hereinbefore defined.

AGENTS OF THE INVENTION which are pharmaceutically acceptable acid addition salts exhibit the same order of activity and tolerability as compounds of formula I as hereinbefore defined, or physiologically-hydrolyzable and -acceptable esters thereof.

The preferred ACTIVE AGENT OF THE INVENTION is the compound of example 1. Specific results for this compound in hydrogen-oxalate salt form in one series of experiments performed in accordance with test methods described above are as follows:

TEST A: $IC_{50}$ (PDE IV)=0.0029±0.0012 µM

TEST B: $IC_{50}$=0.06±0.03 µM

TEST C: $IC_{50}$=ca. 0.1 µM

TEST E: COMPLETE PROTECTION AT 100/µg/kg/min. with no animals dying.

TEST H: $ED_{50}$ vs. ovalbumin @ 1 mg/ml=0.005 mg/kg i.t. $ED_{50}$ vs. ovalbumin @ 1.8 mg/ml=0.05 mg/kg i.t.

TEST J: $ED_{20}$=41.4±9.9 ng/kg

TEST L: $IC_{50}$=0.012±0.009 µM

Results for TEST J above indicate a potency of ca. 3.5× less than that of the established β-agonist bronchodilator drug Albuterol (Merck Index, 11th edition item 209). Indicated dosages for use of the said compound by inhalation as a bronchodilator will accordingly be of the order of ca. 3 to 4× dosages commonly employed in such therapy using Albuterol as therapeutic agent.

I claim:

1. A compound of formula I

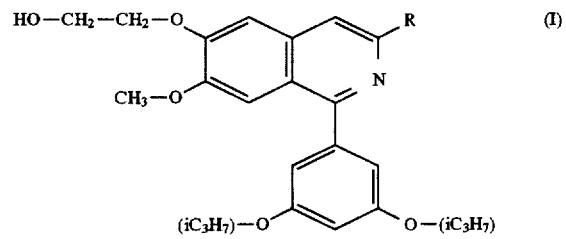

wherein R is ethyl or n-propyl, or a physiologically-hydrolyzable and -acceptable ester thereof, or an acid addition salt of such a compound or ester.

2. The compound according to claim 1 wherein R is ethyl or an acid addition salt thereof.

3. The compound according to claim 1 wherein R is n-propyl or an acid addition salt thereof.

4. A method of treating obstructive or inflammatory airways disease, or for the down-regulation or inhibition of TNF-α release, or for the inhibition of PDE IV isoenzyme activity, or of effecting immunosuppression, or for the treatment of inflammatory disease in a subject in need thereof, which method comprises administering to said subject an effective amount of a compound according to claim 1 or a physiologically-hydrolyzable acid-acceptable ester thereof or a pharmaceutically acceptable acid addition salt of such a compound or ester.

5. A method according to claim 4 for the treatment of asthma.

6. A pharmaceutical composition comprising a pharmaceutically acceptable carrier or diluent and a therapeutically effective amount of a compound according to claim 1, or a physiologically-hydrolyzable and -acceptable ester thereof, or a pharmaceutically acceptable acid addition salt of such a compound or ester.

7. The compound according to claim 2 in free base form.

8. The compound according to claim 2 in hydrochloride form.

9. The compound according to claim 2 in hydrogen fumarate form.

10. The compound according to claim 2 in hydrogen oxalate form.

11. The compound according to claim 2 in hydrogen maleate form.

12. The compound according to claim 3 in free base form.

13. The compound according to claim 3 in hydrogen oxalate form.

14. A compound according to claim 1 wherein the acid addition salt is pharmaceutically acceptable.

15. The compound according to claim 2 wherein the acid addition salt is pharmaceutically acceptable.

16. The compound according to claim 3 wherein the acid addition salt is pharmaceutically acceptable.

* * * * *